(12) United States Patent
Hong

(10) Patent No.: US 8,845,654 B2
(45) Date of Patent: Sep. 30, 2014

(54) SCALED HEAD FRAME POSITIONER AND TABLETOP ADAPTER

(75) Inventor: Linda X. Hong, Larchmont, NY (US)

(73) Assignee: Montefiore Medical Center, Bronx, NY (US)

( * ) Notice: Subject to any disclaimer, the term of this patent is extended or adjusted under 35 U.S.C. 154(b) by 1475 days.

(21) Appl. No.: 12/386,536

(22) Filed: Apr. 20, 2009

(65) Prior Publication Data

US 2010/0268248 A1    Oct. 21, 2010

Related U.S. Application Data

(62) Division of application No. 11/380,797, filed on Apr. 28, 2006, now Pat. No. 7,871,423.

(51) Int. Cl.
| | | |
|---|---|---|
| A61B 19/00 | (2006.01) | |
| A61B 17/00 | (2006.01) | |
| A61F 4/00 | (2006.01) | |
| A61F 5/04 | (2006.01) | |

(52) U.S. Cl.
CPC .................................. *A61B 19/203* (2013.01)
USPC ........................................... 606/130; 606/56

(58) Field of Classification Search
CPC .. A61B 19/5244; A61B 19/203; A61B 19/20; A61N 1/0534; A61N 1/0539
USPC .................................................. 606/56, 130
See application file for complete search history.

(56) References Cited

U.S. PATENT DOCUMENTS

| 4,211,011 A | 7/1980 | Jacobson |
| 4,465,069 A | 8/1984 | Barbier et al. |
| 4,592,352 A * | 6/1986 | Patil .............................. 606/130 |
| 4,617,925 A | 10/1986 | Laitinen |
| 4,868,990 A | 9/1989 | Steinberg |
| 5,171,296 A | 12/1992 | Herman |
| 5,423,832 A * | 6/1995 | Gildenberg ................... 606/130 |
| 5,628,315 A | 5/1997 | Vilsmeier et al. |
| 5,702,406 A | 12/1997 | Vilsmeier et al. |
| 5,855,582 A | 1/1999 | Gildenberg |
| 5,920,998 A | 7/1999 | Slilaty |
| 6,355,049 B1 | 3/2002 | Gill |
| 7,231,723 B1 | 6/2007 | O'Neill et al. |
| 2006/0213521 A1* | 9/2006 | Radney .................... 128/207.11 |
| 2006/0235435 A1 | 10/2006 | Soerensen et al. |
| 2007/0032795 A1 | 2/2007 | Schloesser et al. |

* cited by examiner

*Primary Examiner* — Katherine Dowe
*Assistant Examiner* — Michael Mendoza
(74) *Attorney, Agent, or Firm* — Gerald E. Hespos; Michael J. Porco; Matthew T. Hespos

(57) ABSTRACT

A scaled head frame positioner and tabletop adapter are provided. The positioner may be employed for any neurosurgical procedure that requires fixed positioning of the stereotactic head frame or ring onto a patient's skull. The positioner employs a generally triangular shaped member with Velcro tapes fixed at each corner. The tapes have measurement markings, such as measurement tapes. The positioner supports the head frame with the tapes engaging means on the frame and fastened back to themselves, with markings indicating distances to adjust the position of the frame about the patient's head. Furthermore, the tabletop adapter clamps the patient with a stereotactic head frame onto a CT or treatment table. The tabletop adapter includes a generally U-shaped bracket secured to a support to be placed on the tabletop. The bracket is attachable to the head frame of the patient to hold his head in a desired position.

9 Claims, 5 Drawing Sheets

SCALED HEAD FRAME POSITIONER AND TABLETOP ADAPTER

This is a divisional of application Ser. No. 11/380,797, filed Apr. 28, 2006, now U.S. Pat. No. 7,871,423.

BACKGROUND

1. Field

The present disclosure relates generally to stereotactic framework systems, and more particularly, to a scaled head frame positioner for positioning of a stereotactic frame head ring onto a patient's skull and tabletop adapter to clamp the patient with the stereotactic frame head ring onto a CT or treatment table.

2. Description of the Related Art

Procedures which involve surgery, radiation or other procedures performed on the brain or other intracranial structures are especially hazardous for the patient, because of the extreme sensitivity of brain tissues, the difficulty in identifying and accessing the particular portion of the brain upon which a procedure is to be performed, and the danger of damaging brain tissues which overlie or surround the portion upon which the procedure is to be performed. The desire for precisely locating and accessing interior portions of the brain and other intracranial structures have lead to the development of the neurosurgical subspecialty of stereotactic surgery or "stereotaxis."

Stereotaxis ordinarily involves the use of an external apparatus attached to the patient's skull during presurgical diagnostic procedures and during surgical procedures. The apparatus provides a grid or framework in fixed position relative to the patient's skull which may be used to establish a coordinate system for locating, in a reproducible manner, the precise position of a lesion or other area within the intracranial area. The fixed framework also provides a structure external to the skull to which measuring devices, surgical instruments and the like can be attached and, by appropriate manipulation, positioned so they can be introduced to exact points within the intracranial structure. Surgical or other procedures then can be performed at an exact, predetermined, point within the brain or other tissue. The object of such devices is, ultimately, to permit safe impact at a predetermined location within the intracranial space for purposes such as excision, surgical biopsy, placement of catheters, installation of devices, removal of cysts, tumors or hematomas, or may involve focusing or direction of laser beams, radiation, magnetism or the like for diagnostic or treatment purposes.

The development of CAT scan technology, magnetic resonance imaging (MRI), angiography, digital subtraction angiography (DSA) and similar diagnostic procedures for producing images of structures contained within tissue has been applied to the field of stereotaxis to produce image-directed stereotaxis. A stereotactic apparatus is used in conjunction with advanced diagnostic imaging procedures to produce internal tissue images keyed to a cartesian or polar coordinate system. When the same stereotactic apparatus is utilized during surgery, it is possible to access a precise position inside the brain identified on the diagnostic images on the basis of the same coordinate system. For example, in stereotactic radiosurgery, consisting of a large dose of single fraction irradiation of a small intracranial target with radiation, a head ring of a stereotactic apparatus is positioned on the patient's head to ensure precise immobilization of the patient's head for imaging study and treatment.

Therefore, a need exists for techniques for easily and precisely positioning a head ring or frame of a stereotactic framework system to a patient's head so that the head ring or frame can be applied precisely in an exact position relative to the patient's head.

SUMMARY

A scaled head frame positioner and tabletop adapter are provided. The positioner of the present disclosure may be employed for any neurosurgical procedure that requires fixed positioning of the stereotactic head frame onto the patient's skull. The positioner employs a generally triangular shaped member with Velcro tapes fixed at each corner. The tapes have measurement markings, such as measurement tapes. The positioner supports the head frame with the tapes engaging means on the frame and fastened back to themselves, with markings indicating distances to adjust the position of the frame about the patient's head. Furthermore, the present disclosure provides for a tabletop adapter to clamp the patient with a stereotactic head frame onto a CT or treatment table. Unlike the prior art which uses plastic blocks to support the patient's head with the stereotactic head frame, the tabletop adapter includes a generally U-shaped bracket secured to a support to be placed on the tabletop. The bracket is attachable to the head frame of the patient to hold his head in a desired position.

According to one aspect of the present disclosure, an apparatus for easily and precisely fixing a frame head ring to a patient's head is provided, the apparatus including a rigid ring configured to have substantially the same diameter as the frame head ring, the rigid ring having a top surface and a bottom surface; a plurality of connectors disposed on and projecting from the bottom surface of the rigid ring, the plurality of connectors being adapted to coupled the rigid ring to the frame head ring; a support member for supporting the rigid ring upon the patient's head, the support member being adapted to come into contact with a top of the patient's head; and at least three adjustment members for coupling the rigid ring to the support member, the at least three adjustment members having scaled indicia for precisely adjusting the frame head ring relative to the patient's head.

According to another aspect of the present disclosure, an adapter for fixing a stereotactic frame head ring onto a CT or treatment table is provided, the adapter includes a generally, flat rectangular substrate configured to be disposed on a CT or treatment table and to support the patient on the CT or treatment table, the substrate having a top surface and a bottom surface; at least two connectors disposed on and projecting from the bottom surface of the substrate, the at least two connectors being adapted to coupled the substrate to the CT or treatment table; and a bracket disposed on one end of the substrate having at least two receiving members projecting perpendicular from the top surface of the substrate, the at least two receiving members configured for receiving screws of the head ring for fixing the head ring relative to the CT or treatment table.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
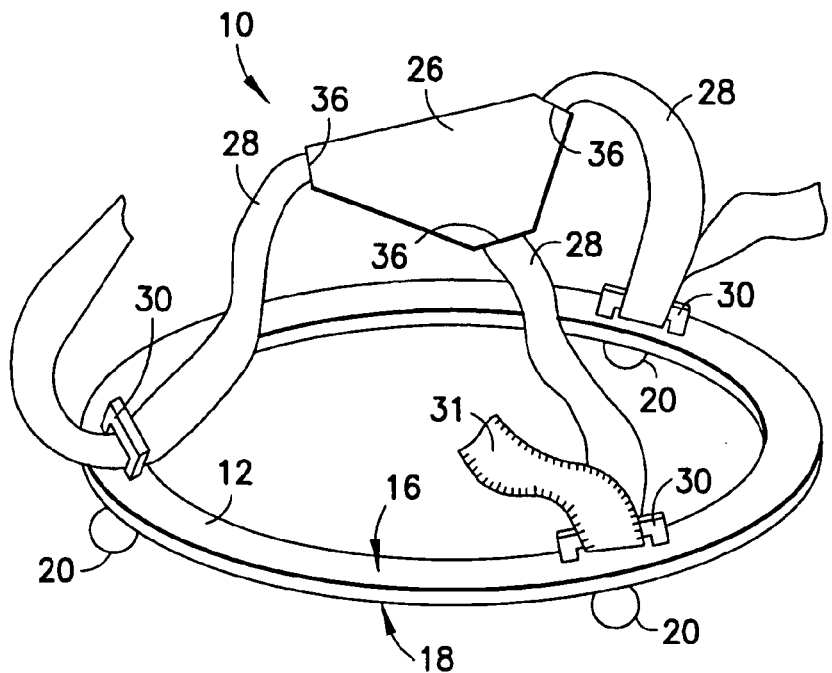
FIG. 1 is a perspective view of a positioner for positioning of a stereotactic head frame onto a patient's skull in accordance with the present disclosure.
Figure 2:
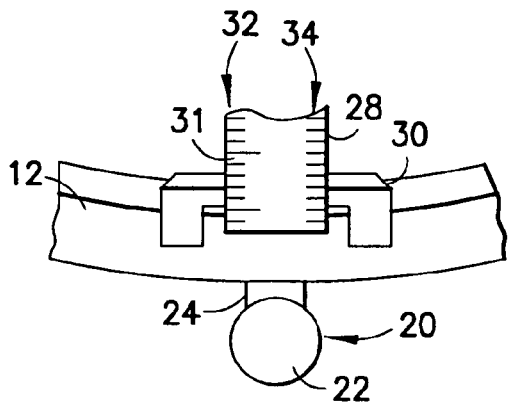
FIG. 2 is a detailed view of a connector of the positioner shown in FIG. 1.
Figure 3:
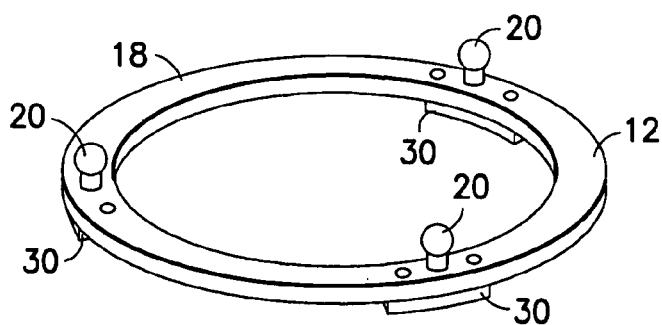
FIG. 3 is a bottom perspective view of the positioner shown in FIG. 1.

Preferred embodiments of the present disclosure will be described hereinbelow with reference to the accompanying drawings. In the following description, well-known functions or constructions are not described in detail to avoid obscuring the present disclosure in unnecessary detail.

A scaled head frame positioner 10 in accordance with the present disclosure is generally shown in FIGS. 1-5. The positioner 10 of the present disclosure will help a user, e.g., a neurosurgeon, to stabilize a stereotactic head frame and to optimize the position of the head frame so that the neurosurgeon can fix the head frame onto the patient's skull with precision and ease. The positioner 10 further provides quantitative indications for adjustment via scaled tapes or straps so the head frame can be applied precisely in an exact position relative to the patient's head.

The positioner 10 includes a rigid ring 12 configured to have substantially the same diameter as the frame head ring 14. The rigid ring 12 is generally flat and includes a top surface 16 and a bottom surface 18. A plurality of connectors 20 are disposed on and projecting from the bottom surface 18 of the rigid ring 12. The plurality of connectors 20 are adapted to coupled the rigid ring 12 to the frame head ring 14 as will be described in more detail in relation to FIG. 4. Each connector 20 includes a ball portion 22 and a stem portion 24.

A support member 26 for supporting the rigid ring upon the patient's head is provided. The support member 26 is configured to come into contact with a top of the patient's head. At least three adjustment members 28 are provided for coupling the rigid ring 12 to the support member 26. The at least three adjustment members 28 have scaled indicia for reproducibly and/or precisely adjusting the frame head ring relative to the patient's head. In one embodiment, each of the adjustment members 28 will include a loop and hook type fastener, e.g., Velcro, on one surface of the adjustment member so the adjustment member 28 may be threaded through bracket 30 of the rigid ring 12 and fasten back upon itself to secure the support member 26 to the ring 12. The adjustment members 28 can take on other forms such as a strap and buckle and the like.

The adjustment members 28 will include on one surface scaled indicia 31. By having scaled indicia on the adjustment members 28 a user can determine settings for a particular patient and make precise adjustments to each adjustment member 28 to precisely position the head ring 12, e.g., to avoid certain features of the patient's head, to rotate the head ring properly, etc. It is to be appreciated that the adjustment members 28 may have one or more measurement system disposed on one surface. For example, on one side of the surface of the adjustment member 28 may display an inch scale 32 while the other side may display a centimeter scale 34. Other measurement scales and systems are contemplated.

In the embodiment shown, the support member 26 is generally triangular but other configurations are contemplated. In this embodiment, the support member 26 has three corners 36 with the adjustment members 28 fixed at each of the corners 36. In this manner, the weight of the head ring 14 is equally distributed and is stable on the patient's head. Other shapes for the support member 26 are contemplated by the present disclosure as along as the adjustment members 28 are equally spaced about the periphery of the support member 26 for stability.

In use, the positioner 10 will be coupled to a head ring 14 and the positioner 10 and head ring 14 will be disposed on the patient's head to fix the head ring to the patient's skull.

Figure 4:
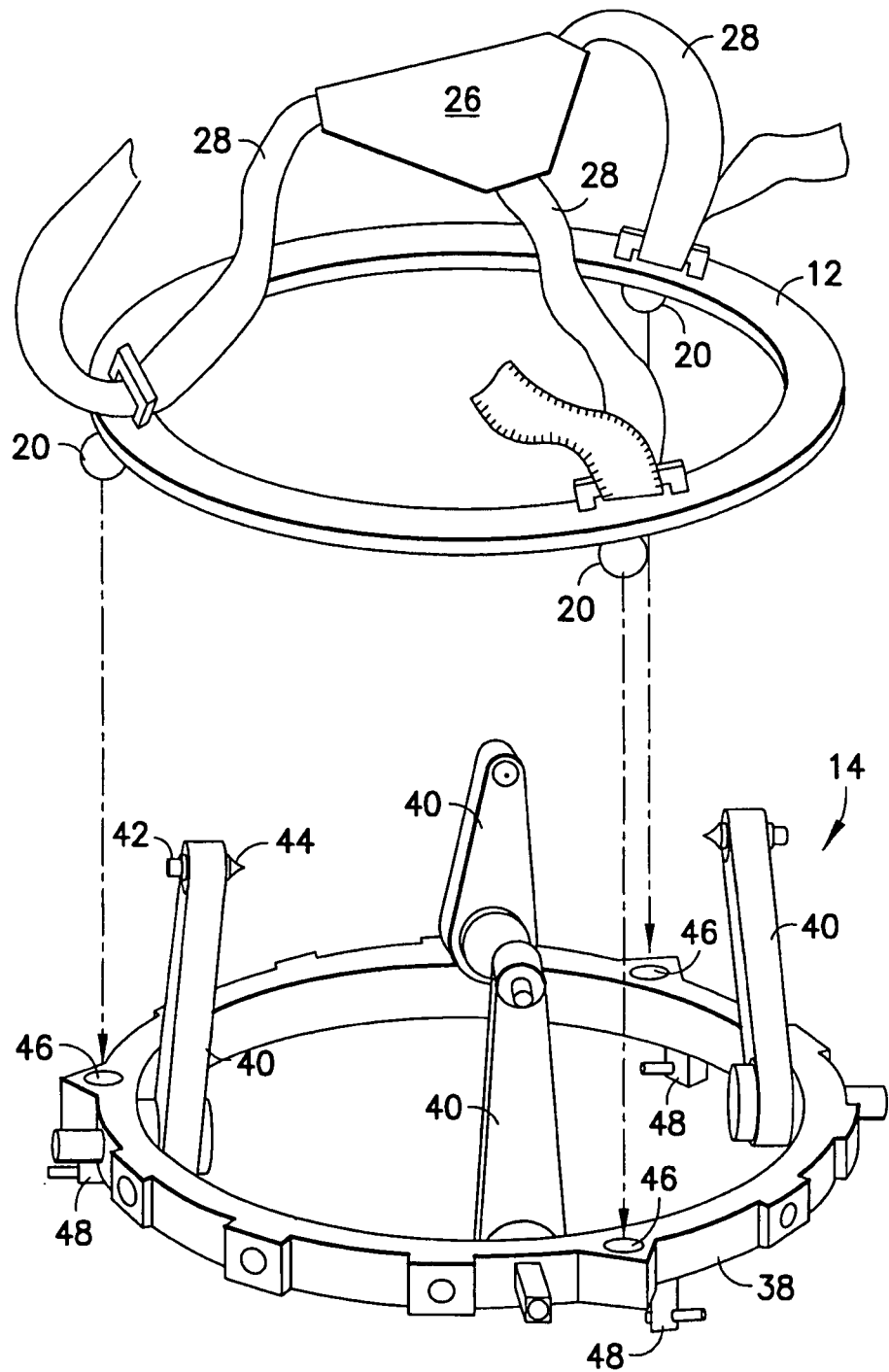
FIG. 4 illustrates a positioner of the present disclosure being coupled to a stereotactic head ring.

Referring now to FIG. 4, there is shown a BRW/CRW-type stereotactic head ring 14 as is known in the art. The head ring 14 comprises an annular base 38, formed of metal. Four vertical brackets 40 extend upward from the inside diameter of the base 38. Four adjustable pins 42 are threadedly engaged with the upper portions of the brackets 40. The pins 42, when rotated relative to the brackets 40, extend inwardly to engage the patient's skull, or retract outwardly to disengage from the patient's skull. The pins 42 have pointed tips or ends 44 which, when the pins are extended inwardly, penetrate the outer tissue of the patient's head and engage the bone of the skull so as to rigidly and invasively affix the head ring 14 to the skull. The pin tips or ends 44 may be removable and replaceable so as to reduce the possibility of spreading infection from one user of the head ring apparatus to the next. If reusable, the pins tips or ends 44 are sterilized after each patient's use.

The head ring 14 includes means for attaching to it other appliances used in stereotactic procedures, e.g., a localizer. As shown, these comprise a plurality, ordinarily three, of recessed ball sockets 46 into which the ball-type connectors of compatible stereotactic appliances may be received. As shown in FIG. 4, the connectors 20 of positioner 10 align with (as indicated by the arrows) and are received by the sockets 46 to fix the positioner to the head ring 14. Spindles 48 extending downwardly from the underside of the head ring 14 are connected to internal means (not shown) in the head ring base 38 for locking in place ball-type connectors 20 received in the sockets 46.

Figure 5:
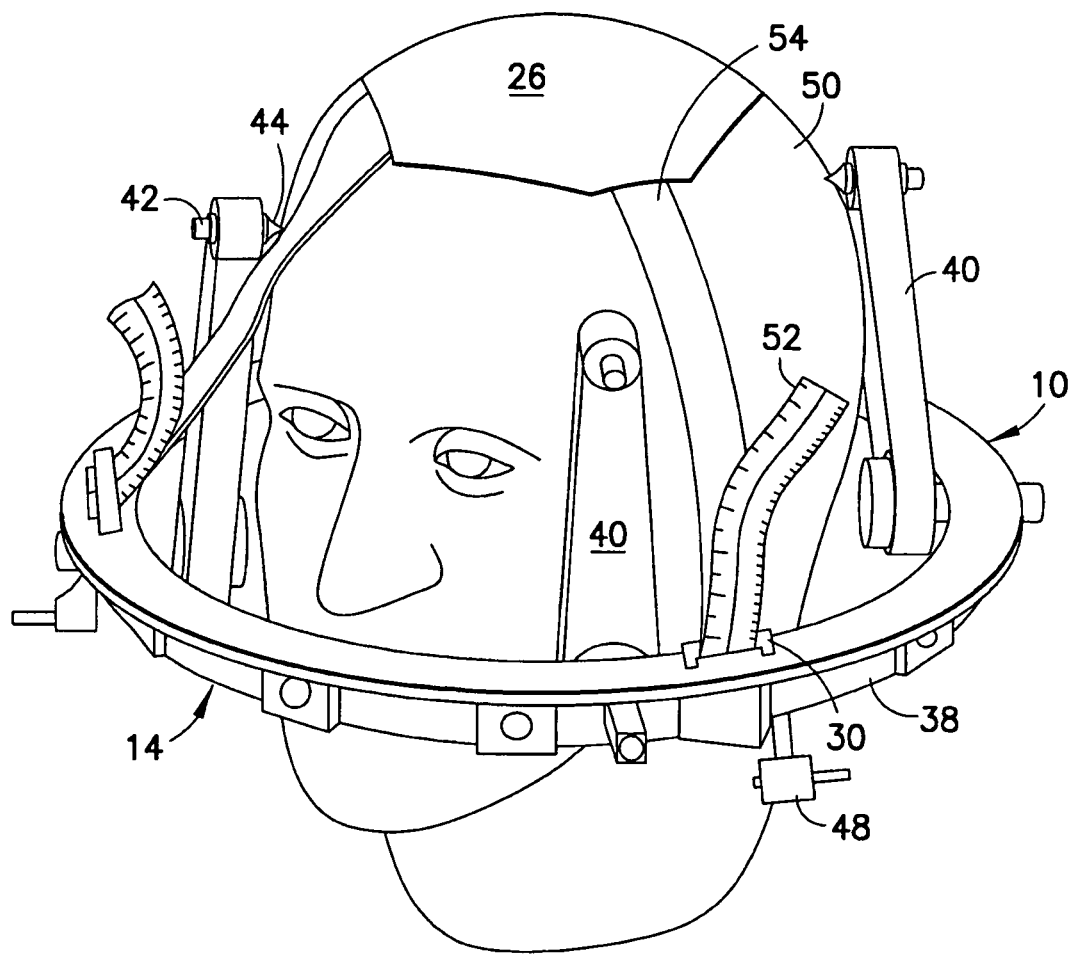
FIG. 5 illustrates the positioner and head ring coupled to a patient's skull.

Referring to FIG. 5, the positioner 10 and head ring 14 are disposed on a patient's head 50. Initially, the support member 26 of the positioner 10 comes into contact with a top potion of the patient's head 50 and generally supports the head ring 14 about the patient's head in a stable manner. The user, e.g., neurosurgeon, can then adjust the position of the head ring 14 and corresponding pin tips or ends 44 relative to the patient's head by adjusting the adjustment members 28. For example, when the adjustment members 28 include hook and loop fasteners, the user can separate an end 52 that has passed through the bracket 30 from the remaining portion 54, adjust the adjustment member 28 accordingly and then reposition the end 52 back onto the other portion 54 of the adjustment member 28. Once the head ring 14 has been set, the pins 42 are adjusted to fix the head ring 14 to the patient's head 50.

The position of the positioner can then be determined by reading the indicia 31 on the adjustment members 28. It is to be appreciated that each of the adjustment members may be adjusted to a different position and thus have a different measurement reading. Once the user is satisfied with the placement of the head ring 14, the positioner 10 can be removed from the head ring 14 by loosening the spindles 48 of the head ring 14. It is to be further appreciated that the positioner 10 of the present disclosure holds the head ring 14 in a steady manner during the positioning process enabling the neurosurgeon to adjust the head ring 14 easily and precisely in any direction.

The stereotactic head ring 14 may be employed to support a localizing device used for establishing a coordinate system and measurement reference for diagnostic procedures and radiation treatment setup. An exemplary localizing device is described in U.S. Pat. No. 5,628,315, the contents of which are incorporated by reference. When diagnostic scanning procedures such as magnetic resonance imagining ("MRI") or computerized axial tomography ("CAT scan") or the like are performed on a patient's head with the localizing device in place, the localizing device provides fixed indicia (fiducials) against which measurements can be made and relative to which a coordinate system can be established for the cranium and intracranial areas. In conjunction with existing computer software developed for the system, the diagnostic images produced from the CAT scan, MRI, etc., performed with the localizing device in place will provide X, Y and Z coordinates (or, in some applications, polar coordinates) for any portion of the patient's skull, brain or other tissue within the cranium which is to be investigated or treated. Such systems make it possible, for example, to identify the location of a tumor, or the like, within the patient's brain by X, Y and Z coordinates which define the position of the tumor, as well as its points of greatest extension within the brain tissue, etc. Since the localizing device is rigidly attached to the head ring 14, which in turn is rigidly attached to the patient's skull 50, the coordinates of diagnostic measurements made utilizing the localizing device may be used directly as coordinates for later surgical, or other treatment, procedures performed utilizing other appliances or instruments rigidly attached to the head ring 14 as long as the head ring remains attached in position to the patient's head.

Figure 6:
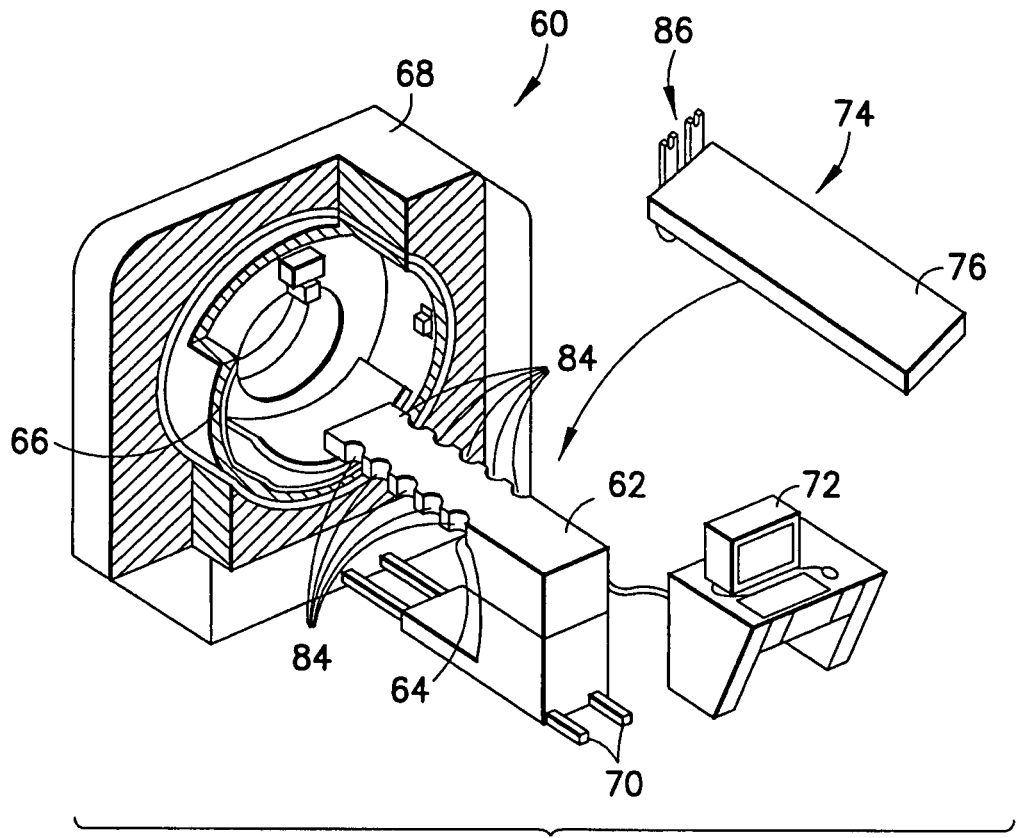
FIG. 6 is a perspective view of a radiation machine and head frame tabletop adapter in accordance with an embodiment of the present disclosure.
Figure 7:
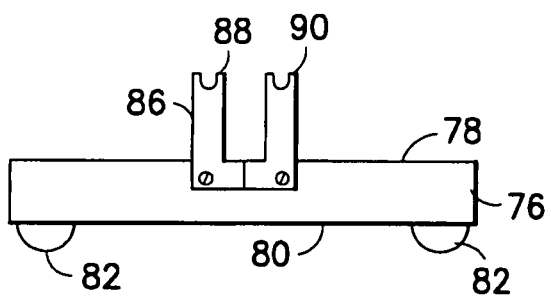
FIG. 7 is an end view of the tabletop adapter shown in FIG. 6.
Figure 8:
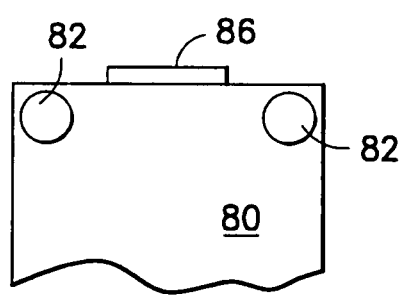
FIG. 8 is a bottom view of the tabletop adapter shown in FIG. 6.

Once the head ring has been secured to the patient, a localizer is then secured to the head ring before a patient is placed in the diagnostic or radiation machine. An exemplary radiation machine is described in U.S. Patent Application Publication No. U.S. 2007/0032795, the contents of which are hereby incorporated by reference. FIG. 1 from U.S. 2007/0032795 has been reproduced here as FIG. 6. Referring now to the drawings, FIG. 6 illustrates a radiation therapy machine 60 suitable for use with the present invention. The radiation therapy machine 60 preferably includes a radiotranslucent couch or treatment table 62 having a cantilevered top 64. The couch top 62 is received within a bore 66 of an annular housing 68 of the radiation therapy machine 60 with movement of the couch 62 along tracks 70 extending along a longitudinal axis translation. The couch 62 is preferably disposed along the longitudinal axis and may slide along that axis through the bore 66 passing first the front surface and then the rear surface. The couch 62 is supported along guide tracks 70 and moved by a motorized drive, such as is well known in the art, so that its position may be controlled by a computer 72. A rotating gantry, coaxial with the bore 66 and positioned within the housing 68, supports an x-ray source and a high energy radiation source on its inner surface.

Conventionally, a plastic block or blocks have been used to support the patient's head with the stereotactic head frame on the couch or treatment table 62. However, the blocks allow the patient's head to move and thus the head frame which may cause misalignment with the coordinate systems. Furthermore, the conventional configuration with the blocks puts a great deal of pressure on for example a plastic CT localizer box. The plastic CT localizer box acts as a weight support for the patient's head. It is foreseeable that repeated pressure on the plastic CT localizer box will ultimately compromise the CT localizer box's integrity. To overcome these deficiencies, a tabletop adapter 74 is provided to fix the head ring on the patient's head to the CT or treatment table 62 which will prevent movement by the patient and relieve unnecessary pressure on the localizing device.

Figure 9:
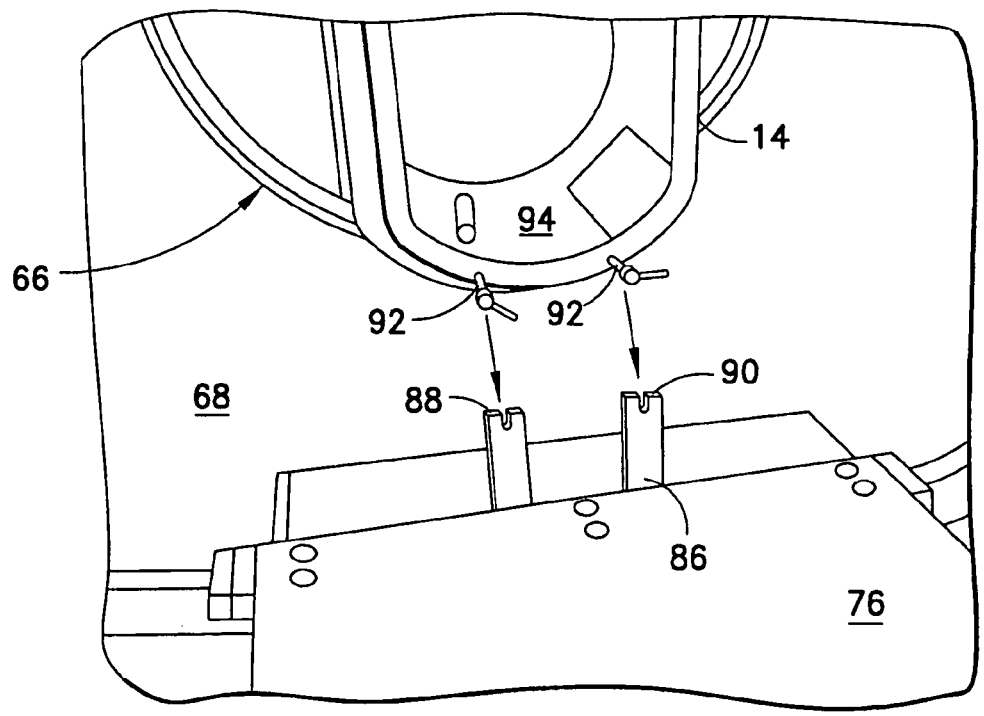
FIG. 9 illustrates the head ring and localizer about to be coupled to the tabletop adapter.
Figure 10:
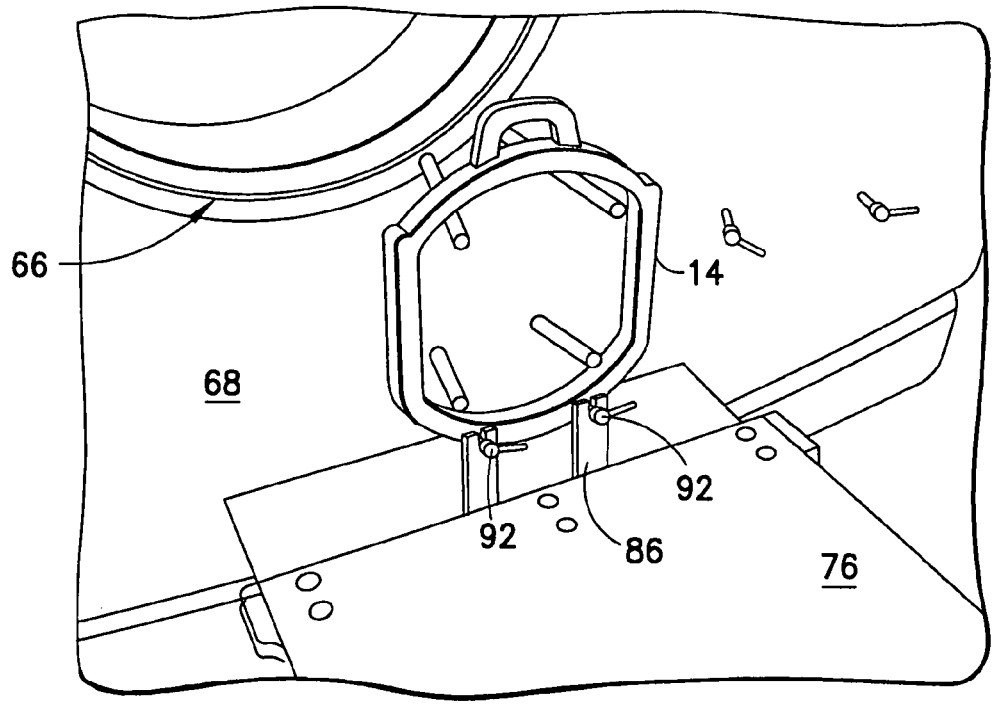
FIG. 10 illustrates the head ring fixed to the tabletop adapter.

Referring to FIGS. 6-10, the adapter 74 includes a generally, flat rectangular substrate 76 configured to be disposed on a treatment table 62 and to support the patient on the treatment table 62. The substrate 76 has a top surface 78 and a bottom surface 80. At least two connectors 82 are disposed on and project from the bottom surface 80 of the substrate 76. The at least two connectors 82 are adapted to couple the substrate 76 to recesses 84 formed along the sides of the treatment table 62. The adapter 76 further includes a U-shaped bracket 86 disposed on one end of the substrate 76 having at least two receiving members 88, 90 projecting perpendicular from the top surface 78 of the substrate 76. The at least two receiving members 88, 90, e.g., semi-circular apertures, are configured for receiving screws of the head frame 14 for fixing the head frame 14 relative to the treatment table 62, as shown in FIGS. 9 and 10.

Referring to FIGS. 9 and 10, the adapter 76 has been fixed to the treatment table 62 by coupling the connectors 82 into the recesses 84 of the table 62. For clarity, the head ring 14 with localizing device 94 is shown without being fixed to a patient's head. The two conical T-bolt screws 92 are aligned with the receiving members 88, 90 of the bracket 86. Once the screws 92 are fully received by the receiving members 88, 90, the screws 92 are clamped down and the head ring 14 is fixed to the adapter 76, and in turn, the head ring 14 is fixed to the treatment couch or table 62. By securing the head ring to the treatment table 62 in this manner, the adapter 76 eliminates any potential patient head movement during treatment, e.g., a CT simulation or radiotherapy treatment. Furthermore, the adapter 76 reduces any additional pressure on the localizing device.

Once the patient is set on the couch or table 62, the patient can be positioned into the bore 66 of the radiation machine 60.

While the disclosure has been shown and described with reference to certain preferred embodiments thereof, it will be understood by those skilled in the art that various changes in form and detail may be made therein without departing from the spirit and scope of the disclosure as defined by the appended claims.

What is claimed is:

1. A system for fixing a patient's head to a table for supporting a patient during a stereotactic procedure, the system comprising:
   a frame head ring having a selected diameter for positioning around a patient's head;
   an apparatus for easily and precisely fixing a frame head ring to a patient's head, the apparatus comprising:
      a rigid ring configured to have substantially the same diameter as the frame head ring, the rigid ring having a top surface and a bottom surface;
      a plurality of connectors disposed on and projecting from the bottom surface of the rigid ring, the plurality of connectors being adapted to coupled the rigid ring to the frame head ring;
      a support member for supporting the rigid ring upon the patient's head, the support member being adapted to come into contact with a top of the patient's head; and
      at least three adjustment members for coupling the rigid ring to the support member, the at least three adjustment members having scaled indicia for precisely adjusting the frame head ring relative to the patient's head; and an adapter for fixing a stereotactic frame head ring onto a table for supporting a patient comprising:

a generally, flat rectangular substrate configured to be disposed on a table and to support the patient on the table, the substrate having a top surface and a bottom surface;

at least two connectors disposed on and projecting from the bottom surface of the substrate, the at least two connectors being adapted to coupled the substrate to the table; and a bracket disposed on one end of the substrate having at least two receiving members projecting perpendicular from the top surface of the substrate, the at least two receiving members configured for receiving screws of the frame head ring for fixing the frame head ring relative to the table.

2. The system as in claim 1, wherein the at least three adjustment members are equally spaced about the periphery of the support member.

3. The system as in claim 1, wherein each of the at least three adjustment members are straps including a top surface and bottom surface, wherein at least one of the top and bottom surface includes loop and hook fasteners.

4. The system as in claim 1, wherein the scaled indicia on each of the at least three adjustment members includes at least two different measurement systems.

5. The system as in claim 1, wherein the plurality of connectors are ball type connectors.

6. The system as in claim 1, wherein the top surface of the rigid ring includes at least three brackets for coupling the at least three adjustment members to the rigid ring.

7. The system as in claim 1, wherein the support member is generally triangular shaped and each of the at least three adjustment members are fixed at each corner of the triangular shaped member.

8. The system as in claim 1, wherein the bracket is a U-shaped bracket including two semi-circular apertures disposed an upper end of the bracket.

9. The system as in claim 1, wherein the at least two connectors are configured to mate with at least two recesses of the table.

* * * * *